(12) United States Patent  
Miwa

(10) Patent No.: US 7,320,518 B2
(45) Date of Patent: Jan. 22, 2008

(54) OPHTHALMIC APPARATUS

(75) Inventor: Tetsuyuki Miwa, Nukata-gun (JP)

(73) Assignee: Nidek Co., Ltd., Gamagori (JP)

( * ) Notice: Subject to any disclaimer, the term of this patent is extended or adjusted under 35 U.S.C. 154(b) by 380 days.

(21) Appl. No.: 11/038,527

(22) Filed: Jan. 21, 2005

(65) Prior Publication Data

US 2005/0162611 A1 Jul. 28, 2005

(30) Foreign Application Priority Data

Jan. 27, 2004 (JP) ............... 2004-019078

(51) Int. Cl.
*A61B 3/10* (2006.01)
*A61B 3/00* (2006.01)

(52) U.S. Cl. ..................... 351/206; 351/200
(58) Field of Classification Search ........... 351/206
See application file for complete search history.

(56) References Cited

U.S. PATENT DOCUMENTS 6,236,459 B1 * 5/2001 Negahdaripour et al. ... 356/496
6,299,305 B1 10/2001 Miwa
6,394,603 B2 5/2002 Miwa et al.
2003/0156256 A1 * 8/2003 Takeuchi et al. ........... 351/205

FOREIGN PATENT DOCUMENTS

| JP | A 09-201334 | 8/1997 |
| JP | A 2000-237135 | 9/2000 |
| JP | A 2000-287930 | 10/2000 |
| JP | A 2001-258842 | 9/2001 |
| JP | A 2001-309889 | 11/2001 |

* cited by examiner

*Primary Examiner*—Jordan Schwartz
*Assistant Examiner*—James C Jones
(74) *Attorney, Agent, or Firm*—Oliff & Berridge, PLC

(57) ABSTRACT

An ophthalmic apparatus comprising: an illuminating optical system which projects light to an examinee' eye; an image pickup unit which color-photographs an interference image caused by interference of light reflected by a tear layer of the eye; and an analyzing part which dissolves the photographed interference image to a plurality of color components, determines an appearance of interference stripes of each color component based on a signal of each color component, and obtains a value indicating a dry eye symptom based on at least one of the number of interference stripes of each color component and changes in signal level of each color component.

5 Claims, 4 Drawing Sheets

OPHTHALMIC APPARATUS

BACKGROUND OF THE INVENTION

1. Field of the Invention

The present invention relates to an ophthalmic apparatus for examining a state of the tear layer of an examinee's eye and more particularly to an ophthalmic apparatus for examining (measuring) dry eye symptoms.

2. Description of Related Art

An ophthalmic apparatus for quantitatively examining (measuring) dry eye symptoms has been proposed by, for example, Japanese Patent unexamined publication No. 2000-287930. This ophthalmic apparatus projects illumination light to an examinee's eye and photographs (picks up) an interference image due to interference between light reflected by the surface of an oil layer (film) which is the uppermost surface layer (film) of a tear layer (film) on a cornea and light reflected by the rear files of the oil layer to obtain a grade value indicating the dry eye symptom from its light intensity.

However, because interference stripes (fringes) of diversified (various) colors appear on the photographed interference image depending on the state of the tear layer, the dry eye symptom cannot be examined (measured) appropriately if the light intensity is simply referred to without considering these colors.

SUMMARY OF THE INVENTION

The present invention has been made in view of the above circumstances and has an object to overcome the above problems and to provide an ophthalmic apparatus capable of appropriately examining (measuring) of dry eye symptoms.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic apparatus comprising: an illuminating optical system which projects light to an examinee' eye; an image pickup unit which color-photographs an interference image caused by interference of light reflected by a tear layer of the eye; and an analyzing part which dissolves the photographed interference image to a plurality of color components, determines an appearance of interference stripes of each color component based on a signal of each color component, and obtains a value indicating a dry eye symptom based on at least one of the number of interference stripes of each color component and changes in signal level of each color component.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
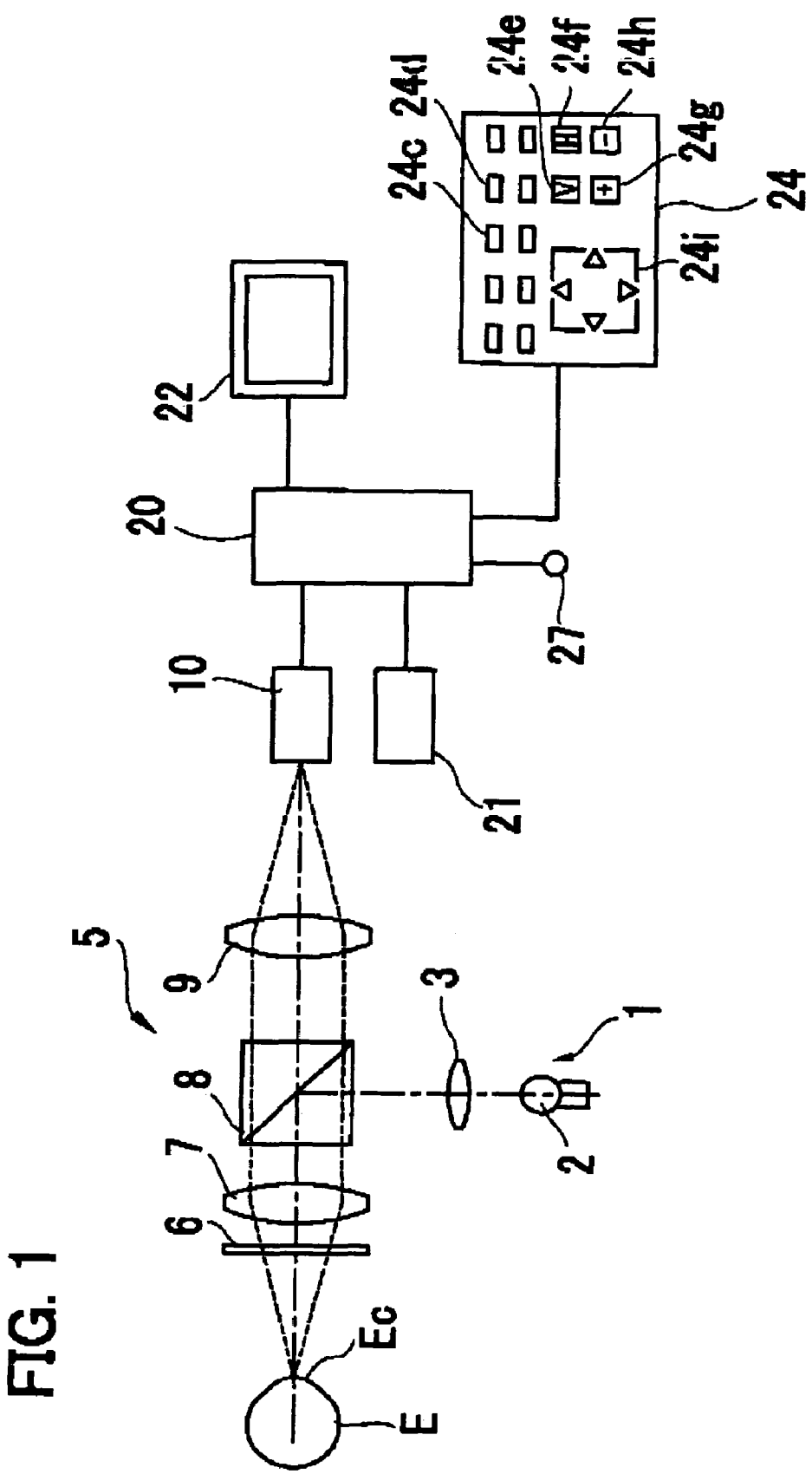
FIG. 1 is a schematic structural view of an optical system and a control system of the ophthalmic apparatus according to the present invention.

Hereinafter, an embodiment of the present invention will be described with reference to the accompanying drawings. FIG. 1 is a schematic structural view of an optical system and a control system of the ophthalmic apparatus according to the present invention.

An illuminating optical system 1 for illuminating the anterior part of an examinee's eye E includes a white light source 2 such as a halogen lamp and a projection lens 3, which are disposed on an optical axis of the optical system 1. An image pickup optical system 5 for photographing up) an image of the anterior part of the eye E includes a ¼ wave plate 6, an objective lens 7, a polarization beam splitter 8, an image forming lens 9 and a color CCD camera 10, which is an image pickup unit, these components being disposed on an optical axis of the optical system 5. The camera 10 photographs (picks up) an interference image due to interference between light reflected by the surface of an oil layer (film) of a tear layer (film) on a cornea Ec of the eye E and light reflected by the rear face of the oil layer (described later).

White illumination light projected by the light source 2 enters the beam splitter 8 through the lens 3. The beam splitter 8 has the property of reflecting an S-polarized component while allowing a P-polarized component to pass therethrough. The S-polarized component of the light entering the beam splitter 8 is reflected toward the eye E. The S-polarized light reflected by the beam splitter 8 enters the ¼ wave plate 6 through the lens 7. The ¼ wave plate 6 has the property of converting linear polarized light to circular polarized light and converting the circular polarized light to the linear polarized light. The S-polarized light entering the ¼ wave plate 6 is converted to clockwise circular polarized light and projected to the oil layer of the tear layer on the cornea Ec.

The clockwise circular polarized light turns to counterclockwise circular polarized light by reflection on the oil layer and enters the ¼ wave plate 6. The counterclockwise circular polarized light entering the ¼ wave plate 8 is converted to P-polarized light and enters the beam splitter 8 through the lens 7. This light passes through the beam splitter 8 and its image is formed on an image pickup surface of the camera 10 through the lens 9.

Part of the S-polarized light reflected by the beam splitter 8 is reflected toward the camera 10 by tho lens 7. Because this light is the S-polarized light, most of it is interrupted (reflected) without passing through the beam splitter 8. Thus, because no light reflected by the lens 7 enters the camera 10 as disturbing light, no flare is observed.

The color interference image photographed by the camera 10 is inputted to an arithmetic control part 20. An image memory 21 is connected to the arithmetic control part 20 and stores the photographed interference images. The arithmetic control part 20 picks out respective color signals, red (R), green (G), and blue (B) from the interference image stored in the image memory 21 and analyzes dry eye symptoms based on the respective color signals. The interference image photographed by the camera 10 is displayed on a color monitor 22. An analysis result obtained by the arithmetic control part 20 is also displayed on the monitor 22. A switch input part 24 having various switches is connected to the arithmetic control part 20.

If the light source 2 is turned on, white illumination light emitted by the light source 2 is projected onto the oil layer of the tear layer on the cornea Ec and an interference image due to reflection by the oil layer is photographed by the camera 10 and displayed on the monitor 22. An examiner makes alignment by moving the optical system relative to the eye E so that the anterior part of the eye E is observed in the center of a screen of the monitor 22 and focused. Upon completion of the alignment, the examiner presses an examination start switch 27 and then urges the examinee to blink (wink) his eye (closes the eye and then opens it). The arithmetic control part 20 detects that the eye E is blinked based on an image signal from the camera 10 and automatically starts the examination. The blink can be detected based on a change in the amount of reflection light from the eye E between when the pupil is closed and when the pupil is opened. The blink may be detected by image processing on the anterior part image. For the detection of the blink, the apparatus may additionally include an optical system for projecting light for detecting the blink to the anterior part and an optical system for receiving light reflected by the anterior part. If the eye E blinks more than once successively, the last blink is assumed to be an examination start timing.

The arithmetic control part 20 measures an elapsed time from a certain blink which is an examination start timing and stores an interference image photographed by the camera 10 after a lapse of a predetermined time (for example, five seconds) since the examination start timing into the image memory 21. After that, the arithmetic control part 20 reads out the interference image stored in the image memory 21, dissolves the image to respective color signals, R, G, and B and analyzes the dry eye symptom based on the signal level of each color.

The analysis method of the dry eye symptom will be described. The interference image obtained from a normal eye is substantially uniform in color and there is little color change with time. On the other hand, in the interference image obtained from the dry eye, the interference stripes (fringes) of diversified (various) colors appear as the symptom advances. Therefore, by judging the appearance condition of the interference stripes of each color, the dry eye symptom can be analyzed appropriately.

Upon analysis, an analysis area and an analysis line(s) common to the colors, R, G, and B, are set. Reference numeral 121 in FIG. 2 indicates the analysis area in the interference image. This analysis area 121 can be set variably. If an analysis area setting mode is established by a switch 24c of the input part 24, the analysis area 121 is displayed on the monitor 22. A vertical size and a horizontal size of the analysis area can be changed to a desired size by switches 24e, 24f, 24g, and 24h. The position of the analysis area 121 can be moved to a desired position with a switch 24i. A shape of the analysis area 121 may be of any other shape such as circular shape.

Figure 2:
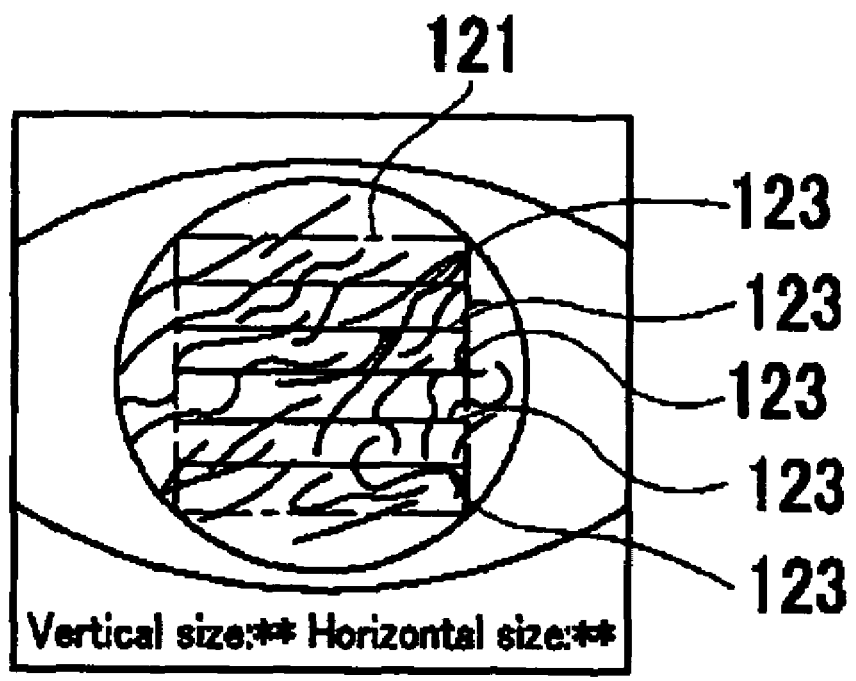
FIG. 2 is view showing an analysis area and analysis lines.

Reference numeral 123 in FIG. 2 indicates an analysis line within the analysis area 121. At least one analysis line 123 is sufficient for the analysis but a plurality of analysis lines 123 are more preferable. Although this embodiment employs the analysis lines extending in the horizontal direction, the analysis lines may be in the vertical direction and further, the analysis lines may be both in the horizontal direction and the vertical direction. Those analysis lines 123 can also be set variably. An analysis line setting mode is established by a switch 24d of the input part 24 and the lines 123 in the horizontal direction are displayed on the monitor 22 by the switch 24f (a line in the vertical direction is displayed by the switch 24e). Consequently, the analysis lines 123 can be moved to a desired position by the switch 24i. If a plurality of analysis lines are used, they are set so as to divide the analysis area 121 equally. Further, a single analysis line may be set if an average value of a plurality of pixels is used. If processing time permits, every line of each pixel may be set as the analysis line.

Figure 3A:
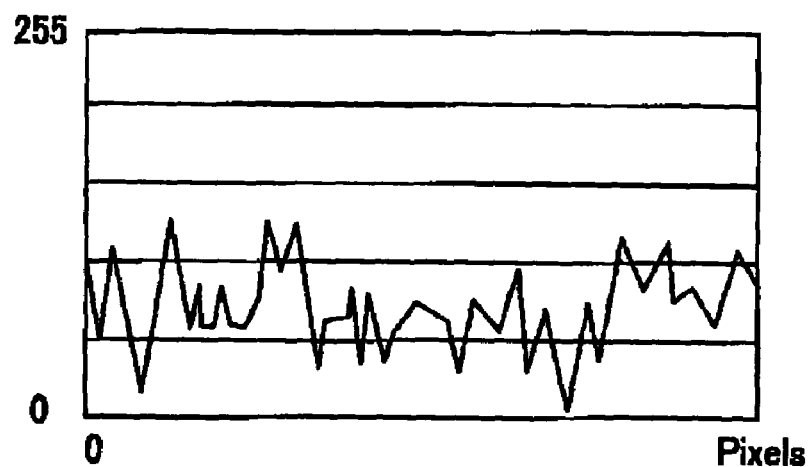
FIGS. 3A to 3C are graphs showing changes in signal level of each color on a certain analysis line.
Figure 3B:
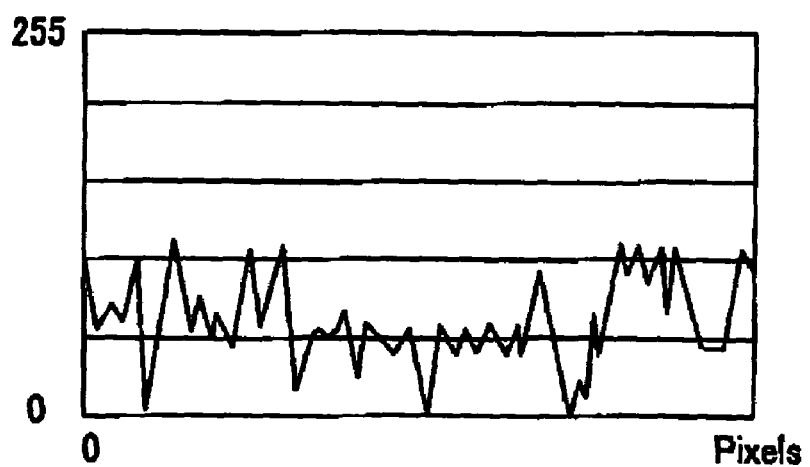
Figure 3C:
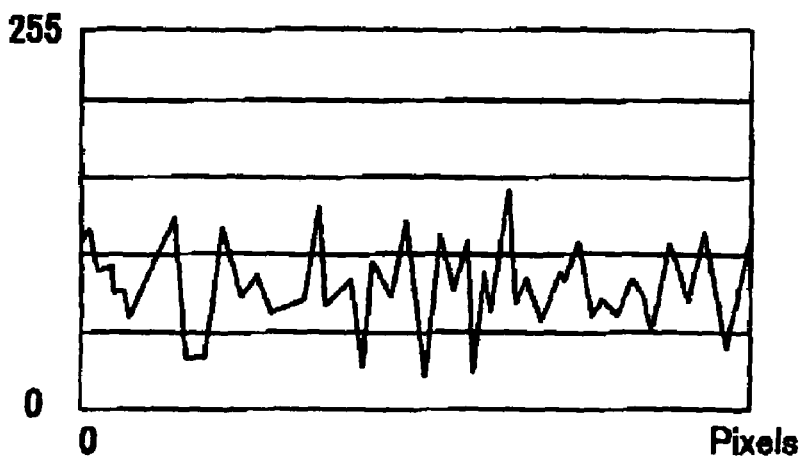

The arithmetic control part 20 extracts the signal level of the analysis line within the analysis area about each dissolved color signal and determines an appearance of the interference stripes of each color based on a change in the signal level of each color. FIGS. 3A to 3C are graphs showing changes in the signal level of each color on a certain analysis line, FIG. 3A, FIG. 3B and FIG. 3C indicate an R signal, G signal, and B signal, respectively. The signal level is presented on 256 sale. If the interference stripes of diversified colors appear, the signal level of each color differs in strength even at the same position. On the contrary if the interference image is considered as just a single intensity signal (density) like a conventional example, there is a high possibility that intensity changes which differ depending on colors may be obscured or unconsidered. As for the signal level of each color, fine noise is removed by smoothing processing or the like.

Figure 4:
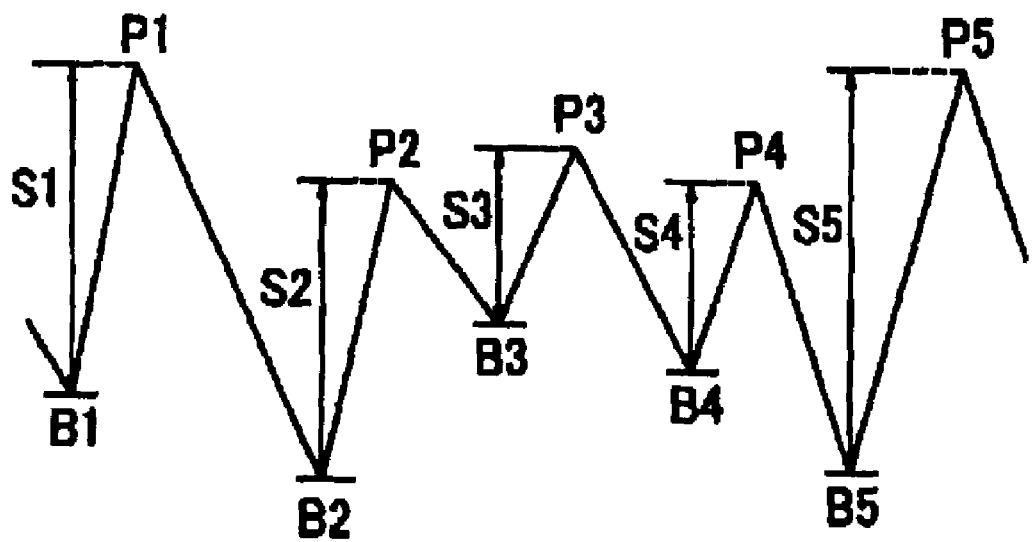
FIG. 4 is an explanatory diagram of a method for determining an appearance of interference stripes of each color based on changes in the signal level of each color.

FIG. 4 is an explanatory diagram of a method for determining an appearance of the interference stripes of each color based on changes in the signal level of each color. In FIG. 4, points B1, B2, B3, . . . (Bn) are bottom inflexion points in which the signal level changes from decrease to increase. Points P1, P2, P3, . . . (Pn) are peak inflexion points in which the signal level changes from increase to decrease. Because when the stripe (fringe) pattern appears, the change (density) in the signal level becomes evident, the appearance of the interference stripes can be determined depending on the peak and bottom states of the changes in the signal level. Specifically, the changes in signal level are viewed from left to right (or from right to left) in FIG. 4 and a scale value Sn between a bottom point Bn and a following peak point Pn is obtained by Sn=Pn−Bn (n=1, 2, 3, . . . ). When this Sn is 50 scale or more, the peak Pn is determined as an interference stripe. The Sn obtained at this time is assumed to be an amplitude value of the change in signal level. Then, the above calculation of Sn and determination of the interference stripes are carried out for all analysis lines.

Calculation of a quantitative value indicating the dry eye symptom is executed as follows. By summing up the number of stripes determined on all the analysis lines for each of R, G, B and dividing this result by the number of the analysis lines, an average number of stripes on one line for each of R, G, B is obtained. Next, by summing up the average number of stripes of each of R, G, B and dividing this result by the number of colors, 3, an average stripe number STav in the analysis area is obtained. This STav is assumed to be a quantitative value indicating the dry eye symptom. For example, if in FIG. 3, it is assumed that the number of stripes of R signal is 5, the number of stripes of G signal is 5, the number of stripes of B signal is 7, each in one line, that is, the number of analysis lines is one, the STav is 5.7. Because the interference stripes of diversified colors often appear as the dry eye symptom advances, the value of the STav increases. On the other hand, the color of the interference image of the normal eye is uniform and the signal level of each of R, G, B is nearly flat and thus the value of the STav decreases.

If the amplitude values Sn of the determined stripes are incorporated into the above calculation of the quantitative value, the dry eye symptom can be quantified more appropriately. By summing up the amplitude values Sn of each stripe determined on all the analysis lines for each of E, G, B an average amplitude value is calculated for each of R, G, B. By multiplying this average amplitude value with the number of stripes and dividing a resulting value by the number of lines, an amplitude value Tr (red), Tg (green), or Tb (blue) of each color are obtained. That is, as for Tr, it is assumed that $$Tr=(\text{number of stripes} \times \text{average amplitude value}/10)/\text{number of lines}.$$

In other words, the "number of stripes×average amplitude value" is the sum of the amplitude values Sn. A number "10" used to divide the averse amplitude value is just a coefficient for calculating the value of a calculation result to a small value and has no special meaning. Tg and Tb are calculated according to the same method. Then, a value T indicating the dry eye symptom is obtained as an average value of three colors, R, G, and B. That is, $Trgb=(Tr+Tg+Th)/3$.

For example, in FIG. 3, assume that for the R signal, the number of stripes is 5 and its average amplitude value is 80, and for the G signal, the number of stripes is 5 and its average amplitude value is 80, and for the B signal, the number of stripes is 7 and its average amplitude value is 70. Further, if it is assumed that the set analysis line is only this one, i.e., the number of analysis lines is ono, Tr is 40, Tg is 40, and Tb is 49. Thus, Trgb is 43.

In an eye of which the dry eye symptom has advanced, the interference stripes of diversified colors appear in an interference image and at the same time the changes in intensity of each color appear strongly. Thus, by incorporating not only the number of stripes but also the amplitude values Sn (the intensity change level) into calculation, the dry eye symptom can be quantified further accurately.

When a tendency of the color of the interference image is considered important in the above-mentioned calculation of STav and Trgb, weighting of each color should be changed. That is, in calculation of Trgb, weighting coefficients KS(red), Kg (green) and Kb (blue) are multiplied with Tr, Tg and Tb. Because in the dry eye, red color and brown color appear frequently in the interference image, for example, the value Kr is set larger than the values Kg, Kb.

The STav and Trgb obtained in the above-described manner are displayed on a monitor 22 together with the interference image to be analyzed. Consequently, the examiner can grasp the dry eye symptom quantitatively.

Although in the above-described description, the interference image photographed after a lapse of a predetermined time from a blink is analyzed, a plurality of interference images photographed at predetermined examination time intervals within a predetermined examination time (duration) from a blink may be analyzed. In this case, the arithmetic control part 20 stores interference images photographed at examination time intervals while measuring an elapsed time from the blink considered as an examination start timing into the image memory 21 successively. For example, if it is assumed that the examination time is 10 seconds and the examination interval is 1 second, 10 pieces of the interference images are photographed and stored. The examination time and examination interval can be set variably by a switch of the input part 24. If the examination time ends, the aforementioned STav and Trgb of each interference image are obtained and then displayed on the monitor 2 in association with the elapsed time. Consequently, changes in the dry eye symptom with time can be checked.

What is claimed is:

1. An ophthalmic apparatus comprising:
    an illuminating optical system which projects light to an examinee's eye;
    an image pickup unit which color-photographs an interference image caused by interference of light reflected by a tear layer of the eye; and
    an analyzing part which dissolves the photographed interference image to a plurality of color components, determines an appearance of interference stripes of each color component based on changes in signal level of each color component on an analysis line within an analysis area of the interference image, and obtains a value indicating a dry eye symptom based on a sum or an average value of at least one of the number of the interference stripes of each color component and the changes in the signal level of each color component on the analysis line.

2. An ophthalmic apparatus comprising:
    an illuminating optical system which projects light to an examinee's eye;
    an image pickup unit which color-photographs an interference image caused by interference of light reflected by a tear layer of the eye; and
    an analyzing part which dissolves the photographed interference image to a plurality of color components, determines an appearance of interference stripes of each color component based on a signal of each color component, and obtains a value indicating a dry eye symptom based on at least one of the number of the interference stripes of each color component and changes in signal level of each color component,
    the analyzing part being arranged to differentiate weighting to each color component when obtaining the value indicating the dry eye symptom.

3. The ophthalmic apparatus according to claim 1, further comprising a blink detecting unit which detects that the eye has blinked,
    wherein the image pickup unit photographs the interference image after a predetermined time from the blink.

4. The ophthalmic apparatus according to claim 1, further comprising a blink detecting unit which detects that the eye has blinked,
    wherein the image pickup unit photographs the interference image at predetermined time intervals within a predetermined time from the blink.

5. A ophthalmic apparatus comprising:
    an illuminating optical system which projects light to an examinee's eye;
    an image pickup unit which color-photographs an interference image caused by interference of light reflected by a tear layer of the eye; and
    an analyzing part which dissolves the photographed interference image to a plurality of color components, determines an appearance of interference stripes of each color component based on changes in signal level of each color component, and obtains a value indicating a dry eye symptom based on a sum or an average value of at least one of the number of the interference stripes of each color component and the changes in the signal level of each color component.

* * * * *